(12) United States Patent
Higashiyama

(10) Patent No.: US 10,773,040 B2
(45) Date of Patent: Sep. 15, 2020

(54) CUFF PRESSURE CONTROLLER DEVICE

(71) Applicant: Murata Manufacturing Co., Ltd., Kyoto (JP)

(72) Inventor: Yuzo Higashiyama, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1365 days.

(21) Appl. No.: 14/919,239

(22) Filed: Oct. 21, 2015

(65) Prior Publication Data
US 2016/0038699 A1    Feb. 11, 2016

Related U.S. Application Data

(63) Continuation of application No. PCT/JP2014/057978, filed on Mar. 24, 2014.

(30) Foreign Application Priority Data

Apr. 24, 2013    (JP) .................................. 2013-091569

(51) Int. Cl.
*A61M 16/04*    (2006.01)
*A61M 16/00*    (2006.01)
(Continued)

(52) U.S. Cl.
CPC ...... *A61M 16/044* (2013.01); *A61M 16/0003* (2014.02); *A61M 16/006* (2014.02);
(Continued)

(58) Field of Classification Search
CPC ............. A61M 16/00; A61M 16/0003; A61M 16/0027; A61M 16/0057; A61M 16/006;
(Continued)

(56) References Cited

U.S. PATENT DOCUMENTS

| | | |
|---|---|---|
| 6,419,462 B1 | 7/2002 | Horie |
| 2004/0013539 A1 | 1/2004 | Takagi |

(Continued)

FOREIGN PATENT DOCUMENTS

| | | |
|---|---|---|
| JP | 2001221163 A | 8/2001 |
| JP | 2007-198147 A | 8/2007 |

(Continued)

OTHER PUBLICATIONS

International Search Report issued in Application No. PCT/JP2014/057978 dated Apr. 22, 2014.

(Continued)

*Primary Examiner* — Colin W Stuart
(74) *Attorney, Agent, or Firm* — Pearne + Gordon LLP

(57) ABSTRACT

A cuff pressure controller device (100) is connected to a foregoing cuff (10) via an air supply tube (125). The cuff pressure controller device (100) includes a controller unit (111), a cuff pressure detector unit (113), a driver circuit (119), a piezoelectric pump (101), a check valve (121), and a release valve (122). The cuff pressure detector unit (113) detects the cuff pressure of the cuff (10). The driver circuit (119) drives the piezoelectric pump (101) at a drive frequency of 20 kHz or higher. The controller unit (111) controls the cuff pressure detector unit (113), the driver circuit (119), and the release valve (122) in such a way that the cuff pressure stays within a predetermined range based on detection results of the cuff pressure detector unit (113) and the like.

20 Claims, 9 Drawing Sheets

(51) Int. Cl.
*A61M 25/10* (2013.01)
*F04B 43/04* (2006.01)
*F04B 43/09* (2006.01)
*F04B 17/00* (2006.01)

(52) U.S. Cl.
CPC .... *A61M 16/0057* (2013.01); *A61M 16/0434* (2013.01); *A61M 25/1018* (2013.01); *A61M 25/10181* (2013.11); *A61M 25/10184* (2013.11); *A61M 2016/0027* (2013.01); *A61M 2205/0294* (2013.01); *A61M 2205/07* (2013.01); *A61M 2205/3355* (2013.01); *F04B 17/003* (2013.01); *F04B 43/04* (2013.01); *F04B 43/043* (2013.01); *F04B 43/046* (2013.01); *F04B 43/09* (2013.01); *F04B 43/095* (2013.01)

(58) Field of Classification Search
CPC .......... A61M 16/0063; A61M 16/0066; A61M 16/0072; A61M 16/0075; A61M 16/0078; A61M 16/0081; A61M 16/0434; A61M 16/044; A61M 25/1018; A61M 25/10181; A61M 25/10184; A61M 2025/102; A61M 2205/07; A61M 2205/0294; A61M 2016/0027; F04B 17/00; F04B 17/003; F04B 43/04; F04B 43/043; F04B 43/046; F04B 43/095; F04B 43/09
See application file for complete search history.

(56) References Cited

U.S. PATENT DOCUMENTS

| | | | |
|---|---|---|---|
| 2010/0252048 A1* | 10/2010 | Young | A61M 16/044 |
| | | | 128/207.15 |
| 2010/0260617 A1* | 10/2010 | Haertl | F04B 43/06 |
| | | | 417/53 |
| 2011/0070110 A1 | 3/2011 | Hirata | |
| 2011/0144587 A1* | 6/2011 | Stone | A61M 5/14212 |
| | | | 604/151 |
| 2011/0253750 A1 | 10/2011 | Takeishi | |
| 2013/0323085 A1 | 12/2013 | Hirata | |

FOREIGN PATENT DOCUMENTS

| | | | | |
|---|---|---|---|---|
| JP | 2009243472 A | | 10/2009 | |
| JP | 2011-027079 A | | 2/2011 | |
| JP | 2011-194222 A | | 10/2011 | |
| JP | 2011194222 A | * | 10/2011 | |
| JP | 2011226375 A | | 11/2011 | |
| WO | 2009/145064 A1 | | 12/2009 | |
| WO | WO-2011145544 A1 | * | 11/2011 | ........... F04B 45/047 |
| WO | 2013/054801 A1 | | 4/2013 | |

OTHER PUBLICATIONS

English translation of Written Opinion issued in Application No. PCT/JP2014/057978 dated Apr. 22, 2014.

* cited by examiner

CUFF PRESSURE CONTROLLER DEVICE

BACKGROUND OF THE DISCLOSURE

Field of the Disclosure

The present disclosure relates to cuff pressure controller devices that control the pressure inside the cuff.

Description of the Related Art

In related art, tracheal intubation is well known in medical fields relating to artificial ventilators. In tracheal intubation, a technician such as a medical doctor and the like inserts an intubation tube into trachea of a subject (usually, a human body) from the cavity of mouth or nose to maintain an open airway, and oxygen is sent to lungs via the intubation tube.

When there is a gap between the intubation tube and the inner wall of trachea, secretions such as gastric fluid, saliva, and the like enters trachea, and the subject may be at a high risk of developing ventilator-associated pneumonia (hereinafter, referred to as "VAP"). To block such secretion inflow, a cuff is provided at the outer wall of the intubation tube.

The cuff inflates upon receiving a supply of gas in the cuff. As the cuff inflates, an outer periphery of the cuff comes into contact with the inner wall of trachea and closes trachea. As described above, in related art, airway is secured with the intubation tube while blocking the secretions from entering trachea with the cuff.

In a case where the inner pressure of cuff (hereinafter, referred to as "cuff pressure") goes out of a predetermined range, a following problem is known to occur.

For example, when the cuff pressure exceeds the predetermined range, the inflated cuff also compresses blood vessels of mucosal tissue of trachea. When the blood vessels are compressed, the blood vessels become ischemic. As a result, necrosis, bleeding, and the like are prone to occur.

On the other hand, when the cuff pressure falls below the predetermined range, the inflation of the cuff becomes insufficient. This may create a gap between the outer periphery of the cuff and the inner wall of trachea, and secretions such as gastric fluid, saliva, and the like may enter trachea.

To address this problem, patent document 1 discloses a cuff pressure controller device that controls the pressure inside the cuff so as to stay within a predetermined range.

FIG. 9 is a block diagram depicting the configuration of various features of a cuff pressure controller device 900 according to the patent document 1. The cuff pressure controller device 900 controls the inner pressure of a cuff 90 (hereinafter, referred to as "cuff pressure"). The cuff pressure controller device 900 includes a control system 910 and a cuff pressure regulator unit 920.

The control system 910 includes a controller unit 911, a cuff pressure detector unit 913, and an alarm unit 916. The controller unit 911 controls each unit in the cuff pressure controller device 900 based on the detection results of the cuff pressure detector unit 913.

The cuff pressure detector unit 913 is connected via a cuff pressure detection tube 918 that is connected to a gas supply tube 925. The cuff pressure detector unit 913 detects the cuff pressure of the cuff 90. The controller unit 911 reads out that cuff pressure from the cuff pressure detector unit 913.

The alarm unit 916 is driven by the controller unit 911, and sounds, for example, an alarm to inform the technician of an anomaly of the cuff 90 and the like.

The cuff pressure regulator unit 920 includes a pressure pump 926, a safety valve 927, a unidirectional valve 921, a release valve 922, a flow volume regulator valve 923, and a reservoir tank 924. The pressure pump 926, the unidirectional valve 921, the safety valve 927, the release valve 922, the flow volume regulator valve 923, and the reservoir tank 924 are connected in this order.

The pressure pump 926 is driven by the controller unit 911, and is an electric pump that applies pressure to the cuff 90 via the gas supply tube 925. In the pressure pump 926, the pressure to be applied to the cuff 90 and its speed are set under the control of the controller unit 911. The unidirectional valve 921 is connected to the downstream side of the pressure pump 926, and prevents backward flow of gas from the cuff 90 side to the pressure pump 926.

The release valve 922 opens and closes in response to the control of the controller unit 911. In the opened state, the release valve 922 releases gas inside the cuff 90 to the atmosphere via the gas supply tube 925, and reduces the pressure of the cuff 90.

The flow volume regulator valve 923 regulates the amount of gas to be supplied to the cuff 90 via the gas supply tube 925. The reservoir tank 924 is connected to the downstream side of the flow volume regulator valve 923, and absorbs cuff pressure variation of the cuff 90.

With the foregoing configuration, the cuff pressure controller device 900 includes the flow volume regulator valve 923 between the pressure pump 926 and the cuff 90, and controls the driving of the flow volume regulator valve 923, the pressure pump 926, and the release valve 922 in such a way that the cuff pressure of the cuff 90 stays inside the predetermined range based on detection results of the cuff pressure detector unit 913. Further, the cuff pressure controller device 900 sounds an alarm to inform anomaly using the alarm unit 916 when the cuff pressure does not stay within the predetermined range.

Patent Document 1: Japanese Unexamined Patent Application Publication No. 2011-194222

BRIEF SUMMARY OF THE DISCLOSURE

The capacity of the cuff provided at the intubation tube is small and, for example, about 20 ml. Thus, to control the pressure inside the cuff so as to stay within a predetermined range, the cuff pressure controller device needs to finely regulate the flow volume of gas to be supplied to the cuff.

However, in a case where a related art motor is used as an actuator of the pressure pump 926 in the cuff pressure controller device 900 of the patent document 1, the drive frequency of the pressure pump 926 is 100 Hz or less. Further, the flow volume of gas discharged during one period of pumping at the pressure pump 926 is large. Thus, in the cuff pressure controller device 900, it is difficult to finely regulate the flow volume of gas to be supplied to the cuff 90 using the pressure pump 926.

In view of this, the cuff pressure controller device 900 of the patent document 1 is provided with the flow volume regulator valve 923 between the pressure pump 926 and the cuff 90. In a case where a throttle valve is used in addition to the above, the flow volume may be reduced. However, when the flow volume remains small, it takes time to inflate the cuff for the first time. This requires the adjustment of the throttle valve and the like each time the cuff is inflated, and causes a problem of decreasing work efficiency.

It may be conceivable to replace the flow volume regulator valve 923 with an active control valve such as a solenoid valve and finely regulate the flow volume of gas to be supplied to the cuff 90 by driving it at high speed.

However, in any of these cases, the cuff pressure controller device 900 becomes larger in size by the amount of the flow volume regulator valve 923 that is added. Further, in the cuff pressure controller device 900, it requires the preparation of additional materials for the flow volume regulator valve 923 and the addition of its fabrication process. This contributes to high manufacturing cost. Further, in a case where the active control valve is used, the electric power consumption increases as much as the flow volume regulator valve 923 is driven. Further, the flow volume regulator valve 923 makes a driving sound by driving the flow volume regulator valve 923 at high speed.

Accordingly, an object of the present disclosure is to provide a cuff pressure controller device that reduces the size of device body, reduces the manufacturing cost, reduces the electric power consumption, and silences the sound.

A cuff pressure controller device of the present disclosure includes following configurations to resolve the foregoing issues.

(1) A pump that includes a discharge hole connected to a cuff and discharges gas from the discharge hole to the cuff;

a cuff pressure detector unit that detects pressure inside the cuff;

a driver circuit that drives the pump at a drive frequency of 15 kHz or higher; and a controller unit that controls the driver circuit in such a way that the pressure inside the cuff stays within a predetermined range based on a detection result from the cuff pressure detector unit are included.

The pump in this configuration is driven at the drive frequency not lower than an audible range (20 Hz to 15,000 Hz). On the other hand, as described above, a related art pump that uses the motor drives at a drive frequency of 100 Hz or less. Therefore, for example, in a case where the flow volume of gas to be discharged from the pump of the present configuration is equal to the flow volume of gas to be discharged from the related art pump, the flow volume of gas discharged during one period of pumping by the pump of the present configuration is smaller compared with the related art pump, and is, for example, 1/200 or less.

Thus, the cuff pressure controller device of the present configuration can finely regulate the flow volume of gas to be supplied to the cuff with the pump by controlling the driver circuit with the controller unit. In other words, the cuff pressure controller device of the present configuration needs no flow volume regulator valve.

With the present configuration, the cuff pressure controller device can be reduced in size by the amount of not having the flow volume regulator valve. Further, in the present configuration, it does not require materials for the flow volume regulator valve and its fabrication process. Thus, the manufacturing cost can be reduced. Further, in the present configuration, no flow volume regulator valve is driven. Thus, electric power consumption can be reduced, and no drive sound of the flow volume regulator valve is produced. Still further, the pump is driven at the drive frequency not lower than the audible range. Thus, no drive sound of the pump is produced.

According to the cuff pressure controller device of the present configuration, downsizing of the device body, reduction in the manufacturing cost, reduction in the electric power consumption, and silencing the sound may be achieved.

(2) The flow volume of the gas discharged during one period of pumping by the pump is 1 nl or more and 10 μl or less.

The flow volume of gas discharged during one period of pumping by the pump of the present configuration is smaller compared with the related art pump, and is, for example, 1/200 or less. Thus, the cuff pressure controller device of the present configuration can finely regulate the flow volume of gas to be supplied to the cuff with the pump by controlling the driver circuit with the controller unit.

(3) The drive frequency is preferably a resonant frequency of the pump.

In the present configuration, the pump is driven at the resonant frequency. This improves efficiency. According to the cuff pressure controller device of the present configuration, the electric power consumption can be further reduced.

(4) The pump preferably includes a piezoelectric element as an actuator and a vibration plate that has a first principal surface to which the piezoelectric element is joined. The vibration plate exhibits a bending vibration due to expansion and contraction of the piezoelectric element.

In the present configuration, efficiency is improved by using the piezoelectric element as an actuator. According to the cuff pressure controller device of the present configuration, the electric power consumption can be further reduced.

(5) The controller unit preferably controls the driver circuit at a control frequency that is equal to or less than one-tenth of the drive frequency.

The pump, in some cases, cannot produce a cuff pressure change of a steady-state driving period due to insufficient rising of vibration at first several periods of driving. In such case, a stable cuff pressure change suitable for the control may be obtained by setting a feedback period at more than ten times the drive period of the pump.

(6) A check valve provided between the discharge hole of the pump and the cuff for preventing an outflow of the gas from the cuff to the discharge hole; and a release valve connected to the cuff for releasing the gas filled in the cuff are preferably included.

In the present configuration, in a case where the pressure inside the cuff stays within the predetermined range, an outflow of gas from the cuff can be prevented by the check valve even when the driving of the pump is stopped. Thus, the present configuration eliminates the need of continuous driving of the pump to keep the pressure inside the cuff within the predetermined range. Thus, the electric power consumption can be reduced.

Further, in the present configuration, in a case where the pressure inside the cuff exceeds the predetermined range, the gas inside the cuff is released by opening the release valve. Thus, according to the present configuration, the pressure inside the cuff can be regulated within the predetermined range.

(7) The pump preferably includes a first casing that is joined to the vibration plate and constitutes a pump chamber together with the vibration plate; and a second casing that covers the first casing with a gap therebetween and forms a ventilation path between the first casing and the second casing, wherein the first casing is provided with a ventilation hole that allows inside of the pump chamber to communicate with outside thereof, and the discharge hole is formed in the second casing at an area opposite to the first ventilation hole.

In the present configuration, the vibration plate exhibits the bending vibration due to expansion and contraction of the piezoelectric element when the drive voltage is applied to the piezoelectric element. This bending vibration of the vibration plate causes a periodic change in volume of the pump chamber. As a result, gas outside the pump is drawn into the pump chamber from the first ventilation hole, and gas in the pump chamber is discharged from the first ventilation hole.

In the present configuration, with the gas discharged from the pump chamber via the first ventilation hole, gas existing outside the pump is drawn in via the ventilation path and then discharged from the discharge hole. Thus, the flow volume of the gas discharged from the discharge hole is larger by the amount of flow volume of the gas that is drawn in.

Thus, according to the present configuration, a discharge flow volume per electric power consumption drastically increases. Thus, according to the present configuration, a large discharge flow volume is obtained despite of low electric power consumption.

(8) The pump preferably includes:

a frame plate that surrounds the vibration plate;

a joint portion that joins the vibration plate and the frame plate and elastically supports the vibration plate with respect to the frame plate; and a flexible plate joined to the frame plate so as to oppose a second principal surface of the vibration plate, which is on opposite side of the first principal surface, the flexible plate being provided with a ventilation hole.

In the present configuration, the peripheral portion of the vibration plate is not fixed in a substantial way. Further, the vibration plate exhibits the bending vibration due to expansion and contraction of the piezoelectric element when the drive voltage is applied to the piezoelectric element in the present configuration, and, with this vibration of the vibration plate, the flexible plate also vibrates. This enables to draw gas in from the ventilation hole and discharge from the discharge hole.

Thus, according to the present configuration, loss associating with the vibration of the vibration plate is smaller. This enables to achieve a high discharge pressure and a large discharge flow volume despite of low electric power consumption.

According to the present disclosure, the downsizing of the device body, the reduction in the manufacturing cost, the reduction in the electric power consumption, and the silencing the sound can be achieved.

BRIEF DESCRIPTION OF THE SEVERAL VIEWS OF THE DRAWINGS

FIG. 6A is a view when the volume of a pump chamber increases, and FIG. 6B is a view when the volume of a pump chamber decreases.

DETAILED DESCRIPTION OF THE DISCLOSURE

First Embodiment of the Present Disclosure

A cuff pressure controller device 100 according to the first embodiment of the present disclosure is now described below.

Figure 1:
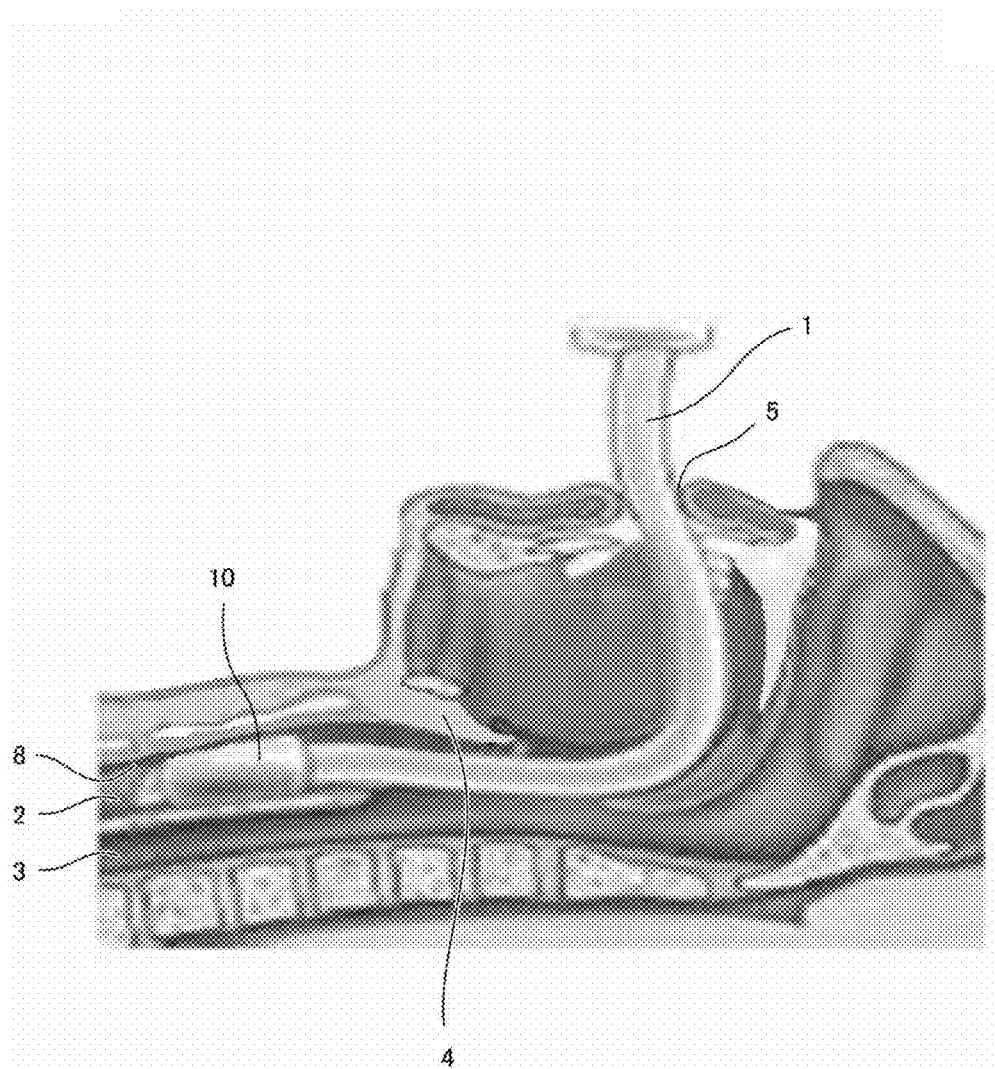
FIG. 1 is a schematic diagram depicting how an intubation tube is inserted into trachea through cavity of mouth.

FIG. 1 is a schematic diagram depicting how an intubation tube is inserted into trachea through cavity of mouth.

In the case where tracheal intubation is performed to secure airway during the usage of artificial ventilators, when there is a gap between an intubation tube 1 inserted through cavity of mouth 5 and an inner wall 8 of trachea 2, secretions from esophagus 3 such as gastric fluid, saliva, and the like enters trachea 2, causing a subject to be at a high risk of developing ventilator-associated pneumonia (hereinafter, referred to as "VAP"). Particularly, during the tracheal intubation, epiglottis 4 is kept open, and gastric fluid from esophagus 3 is likely to enter trachea 2.

To block such secretion inflow, a cuff 10 is provided at a predetermined location of an outer periphery of the intubation tube 1. This cuff 10 inflates when a pressure is applied from outside the body via an air supply tube 125, which will be described below. As the cuff 10 inflates, the outer periphery of the cuff 10 comes into contact with the inner wall 8 of trachea 2 and closes trachea 2.

As described above, airway can be secured with the intubation tube 1 while blocking the secretions from entering trachea 2 with the cuff 10. In the present embodiment, the capacity of the cuff 10 is 20 ml.

Figure 2:
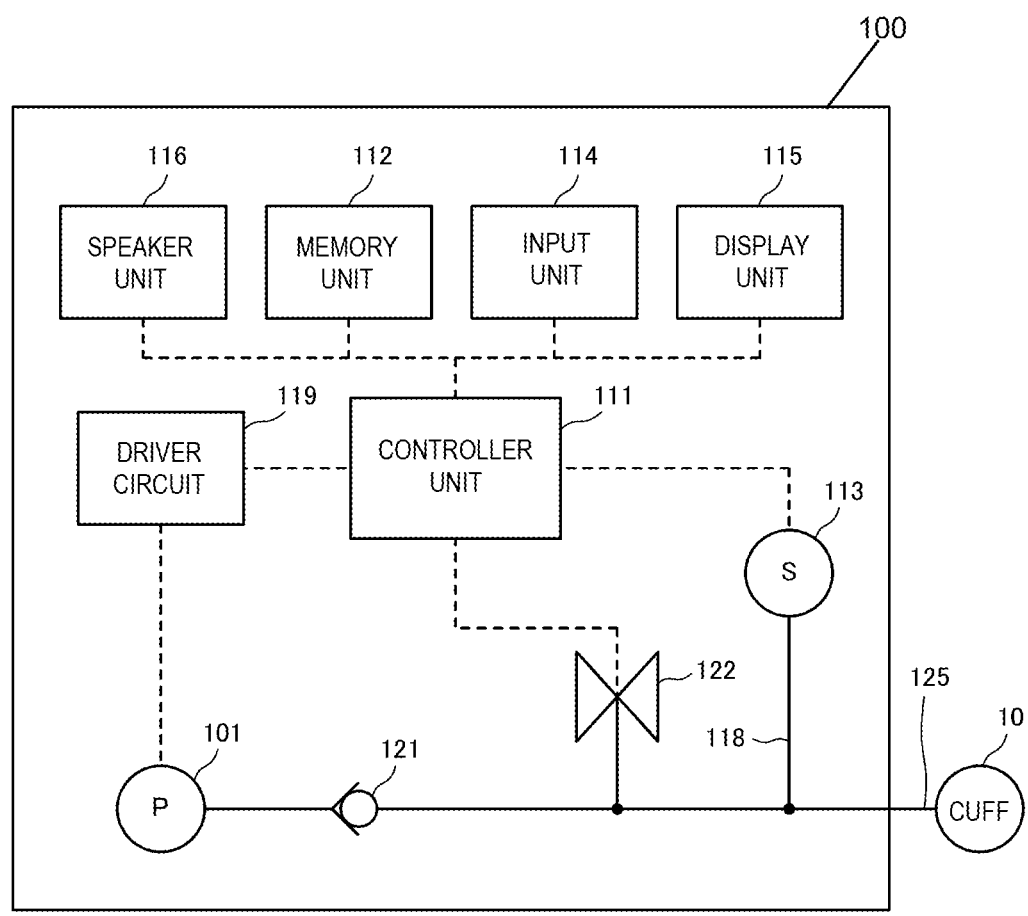
FIG. 2 is a block diagram depicting configuration of various features of a cuff pressure controller device 100 according to a first embodiment of the present disclosure.

FIG. 2 is a block diagram depicting the configuration of various features of the cuff pressure controller device 100 according to the first embodiment of the present disclosure. The cuff pressure controller device 100 is connected to the foregoing cuff 10 via the air supply tube 125. The "cuff pressure" inside the cuff 10 is controlled with the cuff pressure controller device 100.

The cuff pressure controller device 100 includes a controller unit 111, a memory unit 112, a cuff pressure detector unit 113, an input unit 114, a display unit 115, a speaker unit 116, and a driver circuit 119. The cuff pressure controller device 100 further includes a piezoelectric pump 101, a check valve 121, and a release valve 122.

The controller unit 111 controls each unit in the cuff pressure controller device 100. The controller unit 111 has a built-in timer circuit (not illustrated) for measuring time. The controller unit 111 measures time, and obtains time information such as elapsed time and the like.

The controller unit 111 controls the cuff pressure detector unit 113, the driver circuit 119, and the release valve 122 in such a way that the cuff pressure stays inside a predetermined range based on detection results of the cuff pressure detector unit 113 and the like. In the present embodiment, the predetermined range is in a range of 20 cmH$_2$O or more and 30 cmH$_2$O or less.

The cuff pressure detector unit 113 is connected to the cuff 10 via a cuff pressure detection tube 118 that is connected to the air supply tube 125. The cuff pressure detector unit 113 detects the cuff pressure of the cuff 10. The controller unit 111 reads out that cuff pressure from the cuff pressure detector unit 113.

The memory unit 112 is a nonvolatile memory and is composed of, for example, a flash memory or a hard disk drive (HDD). The memory unit 112 stores range information relevant to the predetermined range. Further, the controller unit 111 links information relating to the cuff pressure read from the cuff pressure detector unit 113 and the time information obtained with the timer circuit, and stores them in the memory unit 112 as a temporal change of the cuff pressure. The memory unit 112 further stores information relating to a plurality of pressuring parameters that corresponds to product type of the cuff 10 and the like, information relating to a plurality of operation modes, and the like.

The input unit 114 includes operation buttons and receives input operations of a technician such as a medical doctor and the like. The input unit 114 outputs signals corresponding to the input operations thus received to the controller unit 111.

The display unit 115 is, for example, composed of a liquid crystal display. Upon receiving a display instruction from the controller unit 111, the display unit 115 displays, for example, the information relating to the cuff pressure or the time information on a screen based on display information included in the display instruction.

The speaker unit 116 is, for example, a loudspeaker. The speaker unit 116 is driven by the controller unit 111, and sounds, for example, an alarm to inform the technician such as a medical doctor and the like of anomaly of the cuff 10 and the like.

The driver circuit 119 drives the piezoelectric pump 101 at a drive frequency higher than an audible range (20 Hz to 15,000 Hz). Here, the drive frequency is, for example, 15 kHz to 40 kHz, and is a resonant frequency of the piezoelectric pump 101. Further, the controller unit 111 controls the driver circuit 119 at a control frequency that is equal to or less than one-tenth of the drive frequency.

Here, in some cases, the piezoelectric pump 101 cannot produce a cuff pressure change of a steady-state driving period due to insufficient rising of vibration at first several periods of driving. Thus, to detect stable cuff pressure changes suitable for control at the cuff pressure detector unit 113, the control frequency for controlling the driver circuit 119 is equal to or less than one-tenth of the drive frequency of the piezoelectric pump 101.

The piezoelectric pump 101 includes a discharge hole 24 that is connected to the cuff 10 via the air supply tube 125. The details will be described later. Upon being driven by the driver circuit 119, air is discharged from the discharge hole 24 to the cuff 10 via the air supply tube 125. In the piezoelectric pump 101, the pressure to be applied to the cuff 10, its speed, and the like are set under the control of the controller unit 111.

The check valve 121 is connected between the piezoelectric pump 101 and the cuff 10, and prevents backward flow of air from the cuff 10 to the piezoelectric pump 101. In a case where the cuff pressure stays within the predetermined range, the controller unit 111 can prevents an outflow of gas from the cuff 10 with the check valve 121 even when the driving of the piezoelectric pump 101 is stopped. Thus, such configuration eliminates the need of continuous driving of the piezoelectric pump 101 to keep the cuff pressure within the predetermined range, and can reduce the electric power consumption.

The release valve 122 is connected to the cuff 10. The release valve 122 opens and closes in response to the control of the controller unit 111. In the opened state, the release valve 122 allows the inside the cuff 10 to be communicated with the atmosphere via the air supply tube 125, and allows air inside the cuff 10 to escape. In the close state, the release valve 122 stops allowing the inside the cuff 10 to be communicated with the atmosphere and releasing the cuff 10. In a case where the cuff pressure exceeds the predetermined range, the controller unit 111 allows gas to be released from inside the cuff 10 by opening the release valve 122. This enables the controller unit 111 to regulate the cuff pressure within the predetermined range.

Next, the structure of the piezoelectric pump 101 is described in detail with reference to FIG. 3 to FIG. 5.

Figure 3:
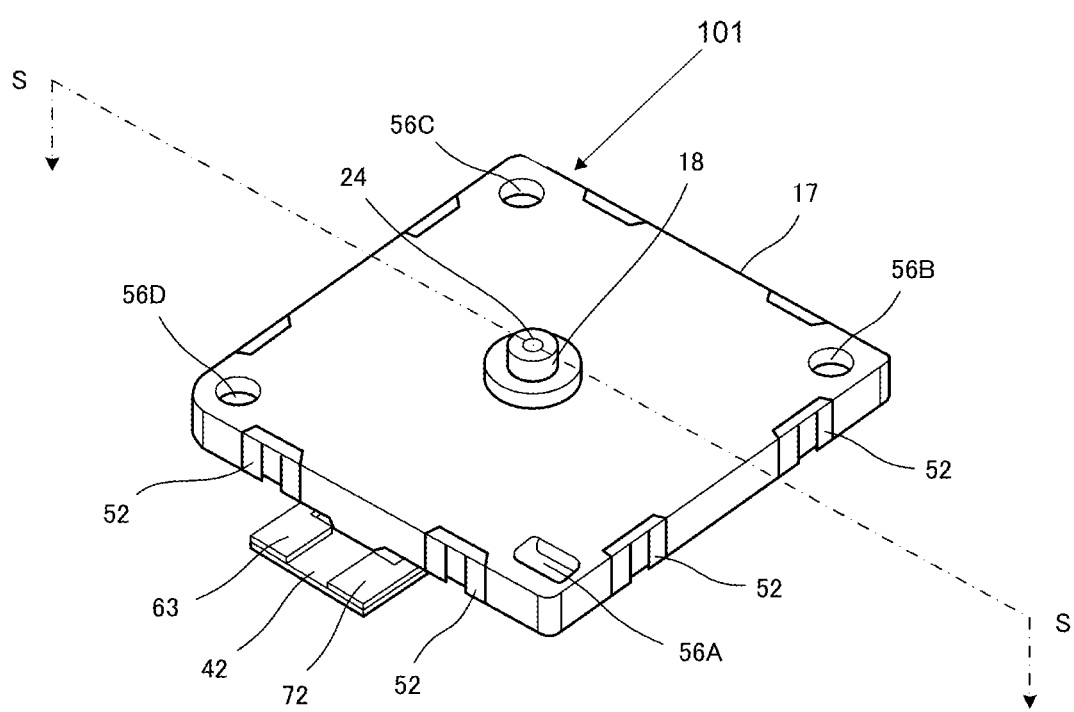
FIG. 3 is an external perspective diagram of a piezoelectric pump 101 included in the cuff pressure controller device 100 depicted in FIG. 2.
Figure 4:
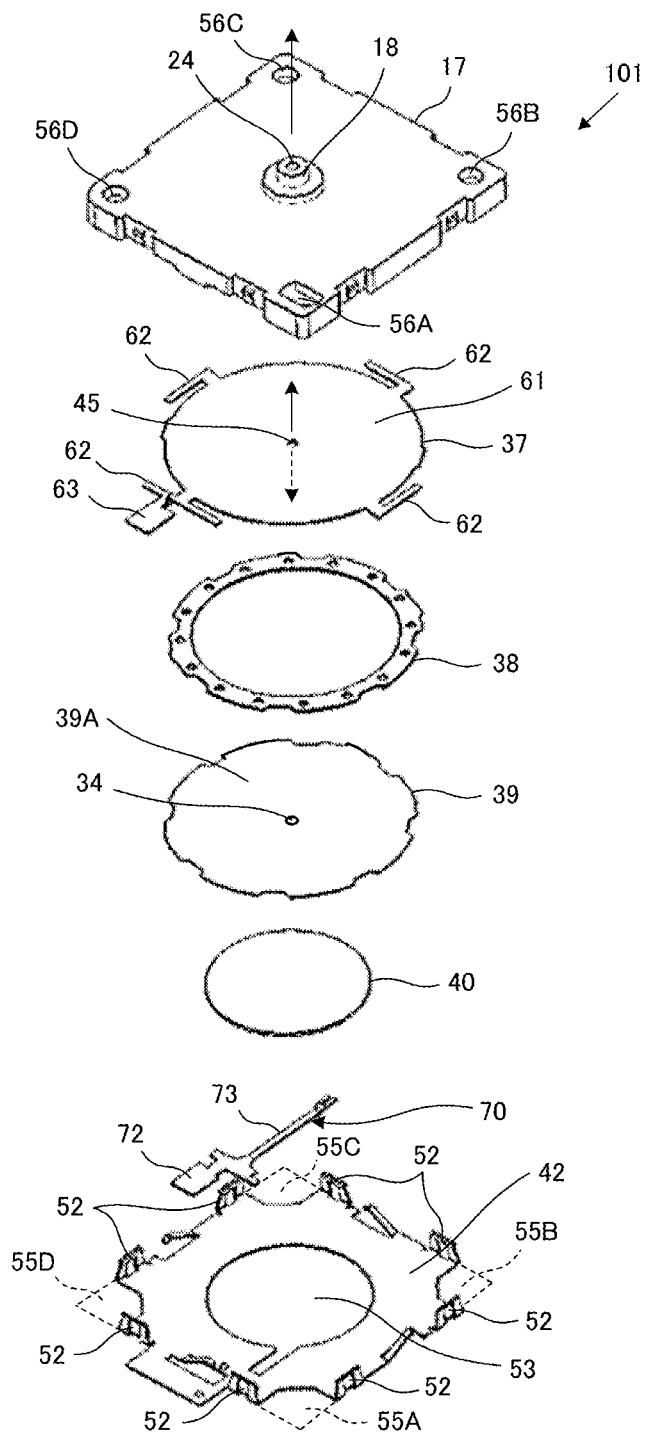
FIG. 4 is an exploded perspective diagram of the piezoelectric pump 101 depicted in FIG. 3.

FIG. 3 is an external perspective diagram of the piezoelectric pump 101 included in the cuff pressure controller device 100 depicted in FIG. 2. FIG. 4 is an exploded perspective diagram of the piezoelectric pump 101 depicted in FIG. 3. FIG. 5 is a cross-sectional diagram of the piezoelectric pump 101 at line S-S depicted in FIG. 3.

The piezoelectric pump 101 includes, from the top, an outer casing 17, a top plate 37, a side plate 38, a vibration plate 39, a piezoelectric element 40, and a cap 42, and has the structure in which these components are stacked in that order. The top plate 37, the side plate 38, and the vibration plate 39 constitute a pump chamber 36. The piezoelectric pump 101 has the dimensions of 20 mm in width×20 mm in length×1.85 mm in height at an area other than a nozzle 18.

The top plate 37 and the side plate 38 constitute a "first casing" of the present disclosure. The outer casing 17 corresponds to a "second casing" of the present disclosure. Further, the top plate 37, the side plate 38, the vibration plate 39, and the piezoelectric element 40 constitute a pump main body.

The outer casing 17 includes the nozzle 18 at the center of which the discharge hole 24 is formed for discharging air, for example. The nozzle 18 has the dimensions of 2.0 mm in diameter of outer shape×0.8 mm in diameter of inner shape (namely, the discharge hole 24)×1.6 mm in height. At four corners of the outer casing 17, screw holes 56A to 56D are formed.

The outer casing 17 has a letter "C" shape cross section whose opened part is directed downward. The outer casing 17 stores the top plate 37 of the pump chamber 36, the side plate 38 of the pump chamber 36, the vibration plate 39, and the piezoelectric element 40. The outer casing 17 is made of, for example, a resin.

The top plate 37 of the pump chamber 36 has a disc shape and is made of, for example, a metal. The top plate 37 is provided with a center portion 61, hook-like projection portions 62 that are projected horizontally from the center portion 61 and come into contact with an inner wall of the outer casing 17, and an outer terminal 63 for making connection with an external circuit.

Further, the center portion 61 of the top plate 37 is provided with a ventilation hole 45 that allows the inside of the pump chamber 36 to communicate with the outside thereof. The ventilation hole 45 is formed at a location opposite to the discharge hole 24 of the outer casing 17. The top plate 37 is arranged on a top surface of the side plate 38.

The side plate 38 of the pump chamber 36 is annular in shape and is made of, for example, a metal. The side plate 38 is arranged on a top surface 39A of the vibration plate 39. Thus, the thickness of the side plate 38 determines the height of the pump chamber 36.

The vibration plate 39 has a disc shape and is made of, for example, a metal. The vibration plate 39 constitutes the pump chamber 36 together with the side plate 38 and the top plate 37.

The piezoelectric element 40 has a disc shape and is made of, for example, lead zirconate titanate based ceramics. The piezoelectric element 40 expands and contracts in response to an alternating current drive voltage applied thereto. The piezoelectric element 40 is arranged on a bottom surface 39B of the vibration plate 39, opposite to the pump chamber 36.

Further, a joined structure of the top plate 37, the side plate 38, the vibration plate 39, and the piezoelectric element 40 is elastically supported by the outer casing 17 with the four projection portions 62 provided at the top plate 37.

An electrode conduction plate 70 is composed of an inner terminal 73 to be connected to the piezoelectric element 40 and an outer terminal 72 to be connected to an external circuit. A tip portion of the inner terminal 73 is solder-bonded to a flat surface of the piezoelectric element 40. A location corresponding to a node of bending vibration of the piezoelectric element 40 is selected as the solder-bonding location. This enables joining the inner terminal 73 and the piezoelectric element 40 without disturbing the bending vibration of the piezoelectric element 40. This enables to suppress vibration of the inner terminal 73.

The cap 42 is provided with a suction opening 53 formed into a disc shape. The diameter of the suction opening 53 is larger than the diameter of the piezoelectric element 40. The cap 42 is further provided with cutouts 55A to 55D at locations corresponding to the screw holes 56A to 56D of the outer casing 17.

Further, the cap 42 includes projection portions 52 projecting toward the top plate 37 side at an outer peripheral border. The cap 42 squeezes and holds the outer casing 17 with the projection portions 52 to pack the top plate 37, the side plate 38, the vibration plate 39 of the pump chamber 36 and the piezoelectric element 40 into the outer casing 17. The cap 42 is made of, for example, a resin.

Figure 5:
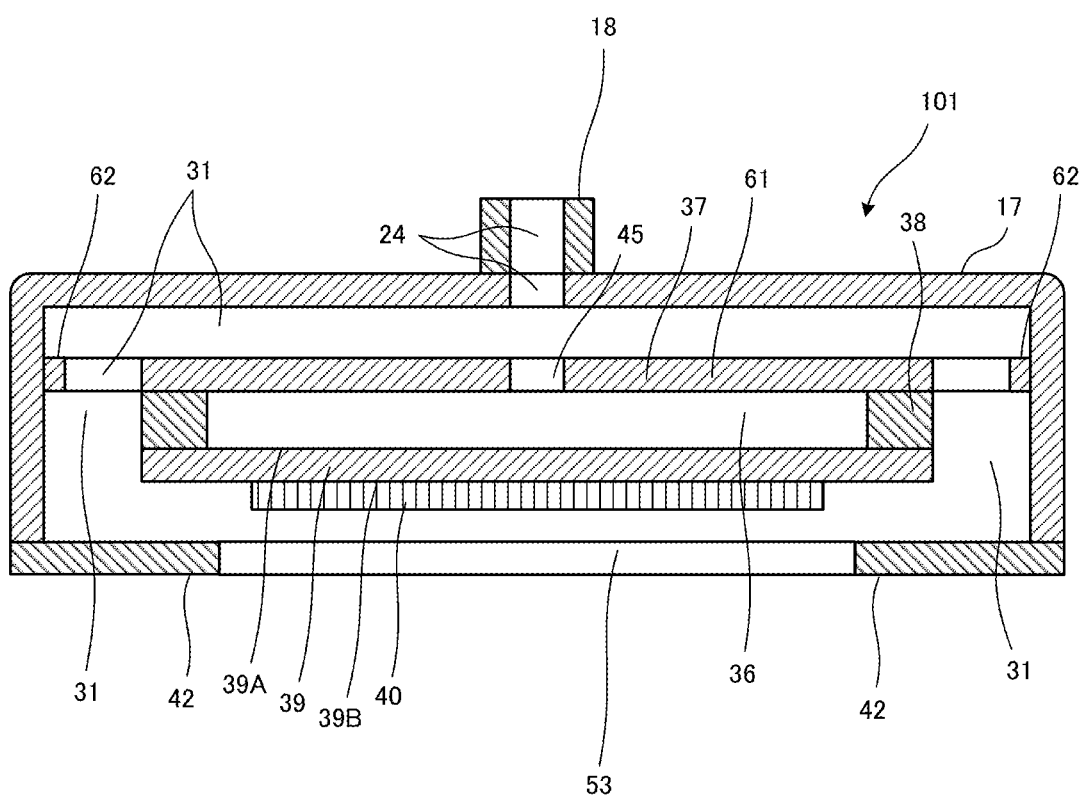
FIG. 5 is a cross-sectional diagram of the piezoelectric pump 101 at line S-S depicted in FIG. 3.

Further, as depicted in FIG. 5, ventilation paths 31 are formed between the outer casing 17 and the cap 42 and the joined structure of the top plate 37, the side plate 38, the vibration plate 39, and the piezoelectric element 40.

Hereinafter, the flow of air during an operation period of the piezoelectric pump 101 is described.

Figure 6:
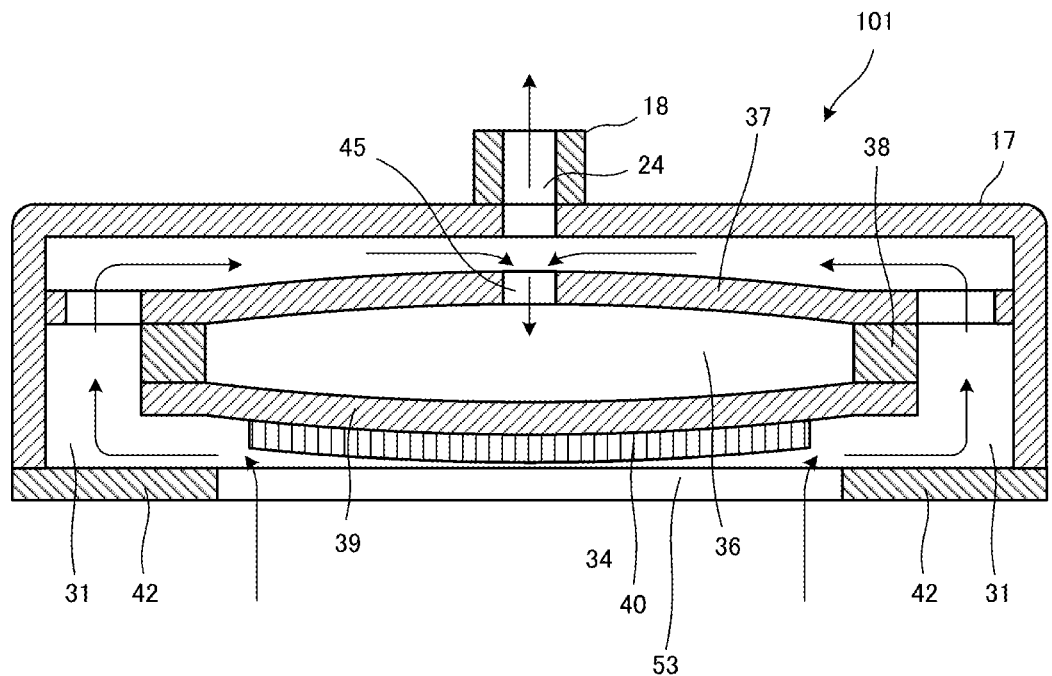
FIGS. 6A and 6B are cross-sectional diagrams of the piezoelectric pump 101 at line S-S depicted in FIG. 3 when the piezoelectric pump 101 depicted in FIG. 3 is driven to resonate at a first-order vibration mode frequency (fundamental wave) of a pump main body.
Figure 6:
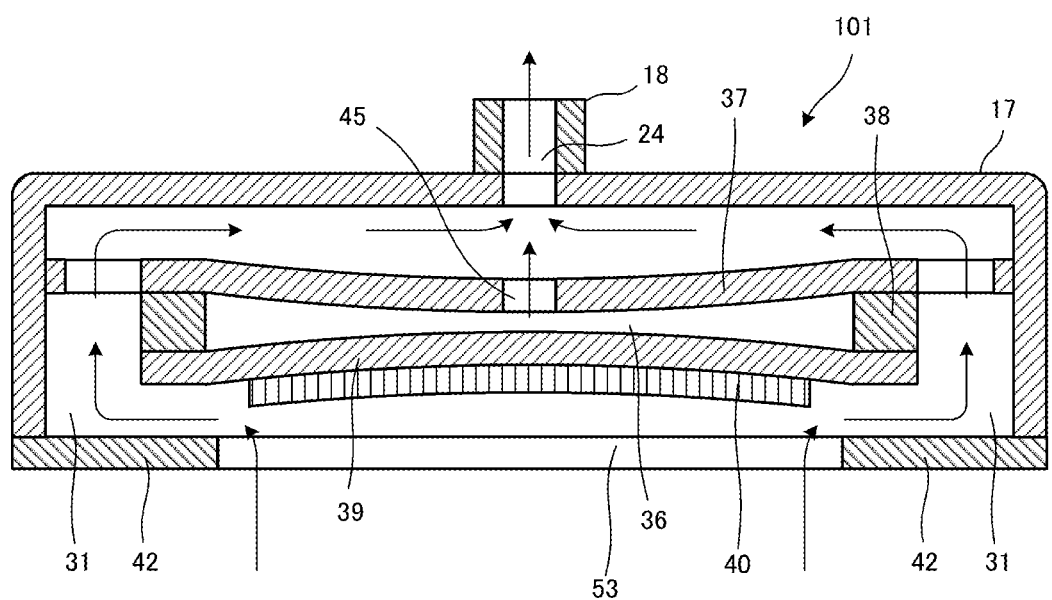

FIG. 6A and FIG. 6B are cross-sectional diagrams of the piezoelectric pump 101 at line S-S depicted in FIG. 3 when the piezoelectric pump 101 depicted in FIG. 3 is driven to resonate at the first-order vibration mode frequency (fundamental wave) of the pump main body. Here, arrows in the drawings represent flows of air.

The vibration plate 39 exhibits a concentric bending vibration when the alternating current drive voltage corresponding to the first-order vibration mode frequency (fundamental wave) of the pump main body is applied to the piezoelectric element 40 from the driver circuit 119 via the outer terminals 63 and 72 in the state depicted in FIG. 5. At the same time, with the bending vibration of the vibration plate 39, the top plate 37 exhibits a concentric bending vibration (in this embodiment, the phase of vibration lags behind by 180 degrees) due to pressure changes in the pump chamber 36 associating with the bending vibration of the vibration plate 39. This causes, as depicted in FIG. 6A and FIG. 6B, bending-deformations at the vibration plate 39 and the top plate 37, and the volume of the pump chamber 36 changes periodically.

As depicted in FIG. 6A, when the alternating current drive voltage is applied to the piezoelectric element 40 and the vibration plate 39 bends toward the piezoelectric element 40 side, the volume of the pump chamber 36 increases. With this, air outside the piezoelectric pump 101 is drawn into the pump chamber 36 via the suction opening 53, the ventilation path 31, and the ventilation hole 45. Although no air flows out from the pump chamber 36, there is inertial force in a flow of air from the discharging hole 24 to outside the piezoelectric pump 101.

As depicted in FIG. 6B, when the alternating current drive voltage is applied to the piezoelectric element 40 and the vibration plate 39 bends toward the pump chamber 36 side, the volume of the pump chamber 36 decreases. With this, air inside the pump chamber 36 is discharged from the discharge hole 24 via the ventilation hole 45 and the ventilation path 31.

At this time, with air being discharged from the pump chamber 36, air outside the piezoelectric pump 101 is drawn in via the suction opening 53 and the ventilation path 31 and discharged from the discharge hole 24. Thus, the flow volume of the air discharged from the discharge hole 24 is larger by the amount of flow volume of the air drawn in from outside.

In this way, according to the piezoelectric pump 101 of the present embodiment, a discharge flow volume per electric power consumption drastically increases. Thus, the piezoelectric pump 101 produces a large discharge flow volume despite of low electric power consumption.

Here, the flow volume of gas discharged during one period of pumping at the piezoelectric pump 101 is smaller than the flow volume of gas discharged during one period of pumping at a related art pump that uses a motor, and is 1/200 or less. The flow volume of gas discharged during one period of pumping at the piezoelectric pump 101 is 1 nl or more and 10 µl or less. In the case where the cuff pressure stays within the predetermined range, the flow volume of gas discharged during one period of pumping at the piezoelectric pump 101 is approximately 0.2 µl. Further, the piezoelectric pump 101 drives at a drive frequency not lower than an audible range (20 Hz to 20,000 Hz). On the other hand, as described above, the related art pump that uses a motor drives at a drive frequency of 100 Hz or less.

Accordingly, the controller unit 111 can finely regulate the flow volume of gas to be supplied to the cuff 10 with the piezoelectric pump 101 by controlling the driver circuit 119 with the controller unit 111 on the order of milliseconds (ms). In other words, the cuff pressure controller device 100 of the present configuration needs no flow volume regulator valve.

For example, in a case where the volume of the cuff 10 is 20 ml, a preset cuff pressure is 25 cmH$_2$O, the drive frequency of the piezoelectric pump 101 is 20 kHz, the discharge flow volume of the piezoelectric pump 101 is 200 ml/min, and the cuff pressure of the cuff 10 is to be increased by 0.1 cmH$_2$O, the required drive time of the piezoelectric pump 101 is 24 milliseconds. Therefore, the piezoelectric pump 101 is required to be able to respond on the order of milliseconds. Since responsiveness of the piezoelectric pump 101 is equal to or less than 1 millisecond, the controller unit 111 has capability of controlling the cuff pressure sufficiently. In other words, the controller unit 111 can regulate the cuff pressure with an accuracy of 0.1 cm H$_2$O using the piezoelectric pump 101.

Accordingly, the cuff pressure controller device 100 can be reduced in size by the amount of an omitted flow volume regulator valve in the cuff pressure controller device 100. Further, in the cuff pressure controller device 100, it does not require the materials for the flow volume regulator valve and its fabrication process. Thus, the manufacturing cost can be reduced. Further, in the cuff pressure controller device 100, no flow volume regulator valve is driven. Thus, electric power consumption can be reduced, and no drive sound of the flow volume regulator valve is produced. Still further, the piezoelectric pump 101 is driven at the drive frequency equal to or higher than the audible range. Thus, no drive sound of the piezoelectric pump 101 is produced.

Thus, according to the cuff pressure controller device 100, the downsizing of the device body, the reduction in the manufacturing cost, the reduction in the electric power consumption, and the silencing the sound can be achieved.

Second Embodiment of the Present Disclosure

A cuff pressure controller device 100 according to the second embodiment of the present disclosure is now described below.

The cuff pressure controller device of the second embodiment differs from the cuff pressure controller device 100 of the first embodiment in having a piezoelectric pump 201 instead of the piezoelectric pump 101. The remaining configuration is the same as that of the first embodiment. Thus, the redundant description is omitted.

The structure of the piezoelectric pump 201 is described in detail with reference to FIG. 7 and FIG. 8.

Figure 7:
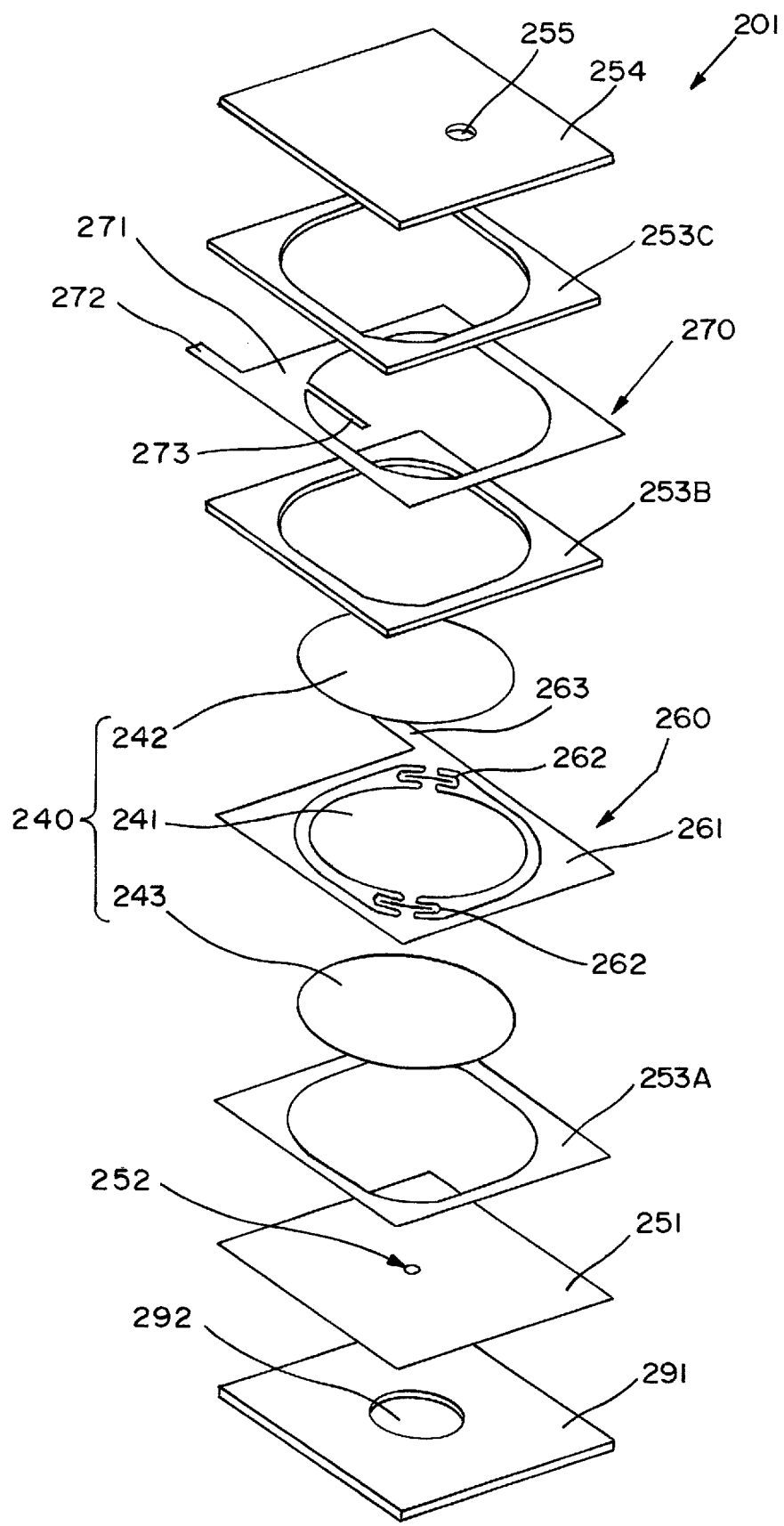
FIG. 7 is an exploded perspective diagram of a piezoelectric pump 201 included in a cuff pressure controller device according to a second embodiment of the present disclosure.
Figure 8:
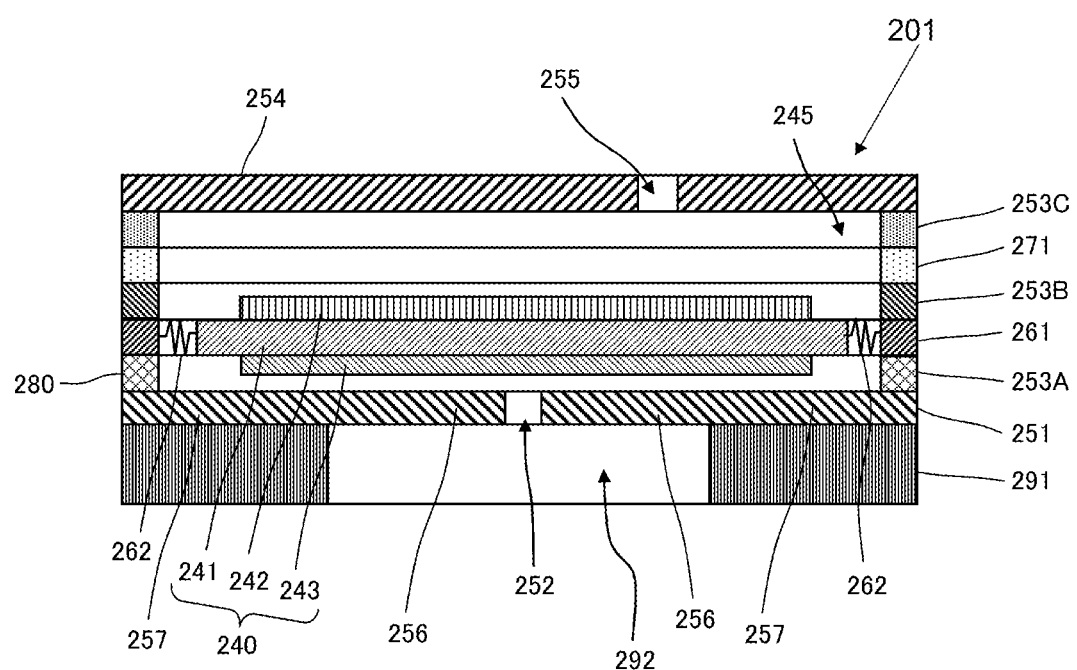
FIG. 8 is a cross-sectional diagram of relevant part of the piezoelectric pump 201 depicted in FIG. 7.
Figure 9:
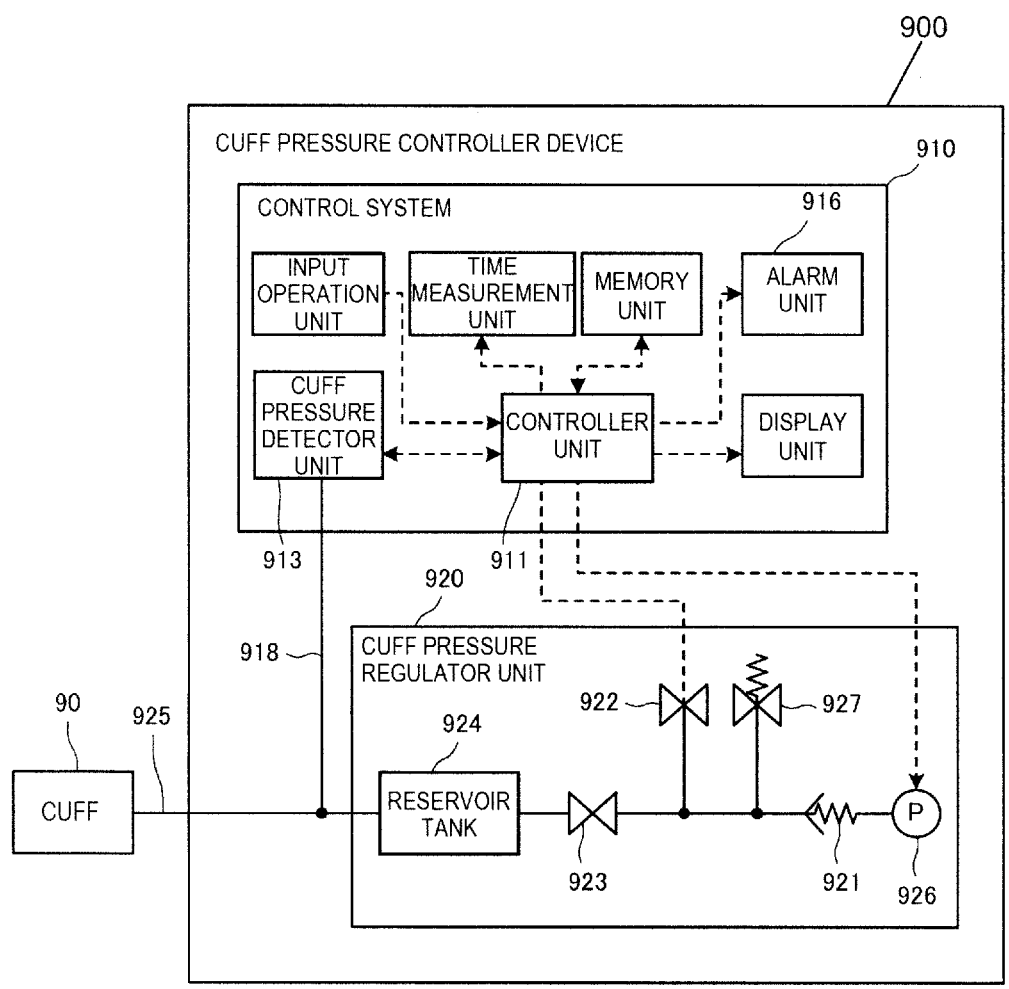
FIG. 9 is a block diagram depicting configuration of various features of the cuff pressure controller device 900 according to the patent document 1.

FIG. 7 is an exploded perspective view of the piezoelectric pump 201 according to the second embodiment of the present disclosure. FIG. 8 is a cross-sectional diagram of relevant part of the piezoelectric pump 201 depicted in FIG. 7.

A substrate 291, a flexible plate 251, a spacer 253A, a reinforcing plate 243, a vibration plate unit 260, a piezoelectric element 242, a spacer 253B, an electrode conduction plate 270, a spacer 253C, and a cover plate 254 are stacked in this order and constitute a pump casing 280. Further, the inner space of the pump casing 280 corresponds to the pump chamber 245.

The piezoelectric element 242 is provided on a top surface of a disc-shaped vibration plate 241. The reinforcing plate 243 is provided on a bottom surface of the vibration plate 241. The vibration plate 241, the piezoelectric element 242, and the reinforcing plate 243 constitute a disc-shaped piezoelectric actuator 240. The piezoelectric element 242 is, for example, made of lead zirconate titanate based ceramics.

Here, the vibration plate 241 may be composed of a metal plate that has larger coefficient of linear expansion than the piezoelectric element 242 and the reinforcing plate 243 and subjected to heat curing at the time of bonding. This allows appropriate compressive stress to remain inside the piezoelectric element 242 without making the piezoelectric actuator 240 warp, and prevents the piezoelectric element 242 from cracking.

For example, the vibration plate 241 may be a material having large coefficient of linear expansion such as phosphor bronze (C5210), stainless steel SUS301 and the like, and the reinforcing plate 243 may be 42 Nickel or 36 nickel or stainless steel SUS430.

With regard to the vibration plate 241, the piezoelectric element 242, and the reinforcing plate 243, they may be arranged in the order of the piezoelectric element 242, the reinforcing plate 243, and the vibration plate 241 from the top. Also in this case, the coefficients of linear expansion are adjusted by selecting the materials to form the reinforcing plate 243 and the vibration plate 241 in such a way that the appropriate compressive stress remains inside the piezoelectric element 242.

A frame plate 261 is provided around the vibration plate 241. The vibration plate 241 is connected to the frame plate 261 via joint portions 262. The joint portion 262 is formed into, for example, a narrow ring shape. The joint portion 262 has an elastic structure with elasticity of a small spring constant. The spacer 253A and the flexible plate 251 are provided to hold the piezoelectric actuator 240 with a constant gap therebetween. The frame plate 261 is provided with an outer terminal 263 for electrical connection.

Accordingly, the vibration plate 241 is elastically supported by the frame plate 261 at two points with the two joint portions 262. Thus, this hardly disturbs the bending vibration of the vibration plate 241.

In the example depicted in FIG. 7, the joint portions 262 are provided at two locations. Alternatively, the joint portions 262 may be provided at three locations or more. Although the joint portion 262 does not disturb the vibration of the piezoelectric actuator 240, it has some effect on the vibration of the piezoelectric actuator 240. Thus, for example, having the joint portions 262 at three locations enables to provide a more natural support and prevent cracking of the piezoelectric element 242.

The vibration plate unit 260 is composed of the vibration plate 241, the frame plate 261, the joint portions 262, and the outer terminal 263. The vibration plate unit 260 is formed by subjecting the metal plates to a punching process.

A spacer 253B is provided on a top surface of the frame plate 261. The spacer 253B is made of a resin. The spacer 253B has the same thickness as the piezoelectric element 242 or thicker. The frame plate 261 electrically insulates the electrode conduction plate 270 from the vibration plate unit 260.

An electrode conduction plate 270 is provided on a top surface of the spacer 253B. The electrode conduction plate 270 is made of a metal. The electrode conduction plate 270 is composed of a frame portion 271 that includes a nearly circular opening, an inner terminal 273 that projects into this opening, and an outer terminal 272 that projects outwardly.

A tip portion of the inner terminal 273 is solder-bonded to a surface of the piezoelectric element 242. A location corresponding to a node of bending vibration of the piezoelectric actuator 240 is selected as the solder-bonding location. This enables joining the inner terminal 273 and the piezoelectric element 242 without disturbing the bending vibration of the piezoelectric element 242. This suppresses vibration of the inner terminal 273.

A spacer 253C is provided on a top surface of the electrode conduction plate 270. The spacer 253C is made of a resin. The spacer 253C has approximately the same thickness as the piezoelectric element 242. The spacer 253C is a spacer for preventing a soldered portion of the inner terminal 273 from contacting with the cover plate 254 when the piezoelectric actuator 240 is vibrating. Further, it prevents a reduction in vibration amplitude due to air resistance when the surface of the piezoelectric element 242 comes exceedingly close to the cover plate 254. Therefore, it is sufficient that the spacer 253C has approximately the same thickness as the piezoelectric element 242.

The cover plate 254 is provided on a top surface of the spacer 253C. The cover plate 254 is provided with a discharge hole 255. The cover plate 254 covers an upper space of the piezoelectric actuator 240. It is not necessary to form the discharge hole 255 at the center of the cover plate 254.

On the other hand, the spacer 253A is provided on a bottom surface of the vibration plate unit 260. In other words, the spacer 253A is interposed between a top surface of the flexible plate 251 and the bottom surface of the vibration plate unit 260. The spacer 253A has a thickness equal to the sum of the thickness of the reinforcing plate 243 and the thickness of about several tens of micrometers. The spacer 253A is a spacer for preventing the piezoelectric actuator 240 from contacting with the flexible plate 251 when the piezoelectric actuator 240 is vibrating.

The flexible plate 251 is provided on a bottom surface of the spacer 253A. A suction hole 252 is formed at the center of the flexible plate 251.

The substrate 291 is provided on a bottom surface of the flexible plate 251. A cylindrical opening 292 is formed at a center portion of the substrate 291. The flexible plate 251 includes a fixed portion 257 that is fixed to the substrate 291 and a movable portion 256 that is placed at a location closer to the inner side than the fixed portion 257 and faces the opening 292.

The movable portion 256 can vibrate at substantially the same frequency as the piezoelectric actuator 240 by means of air pressure variation associating with the vibration of the piezoelectric actuator 240. The movable portion 256 is designed in such a way that a natural frequency of the movable portion 256 is equal to or somewhat lower than the drive frequency of the piezoelectric actuator 240.

Variation in thickness of the gap between the flexible plate 251 and the piezoelectric actuator 240 increases in a substantial way in a case where designing is conducting in such a way that the vibration phase of the flexible plate 251 lags behind the vibration phase of the piezoelectric actuator 240 (for example, lags behind 90 degrees).

Further, the driver circuit 119 depicted in FIG. 2 drives the piezoelectric pump 201 at a drive frequency not lower than the audible range (20 Hz to 15,000 Hz). Here, the drive frequency is a resonant frequency of the piezoelectric pump 201.

Accordingly, the piezoelectric actuator 240 exhibits a concentric bending vibration when the alternating current drive voltage corresponding to the first-order vibration mode frequency (fundamental wave) of the piezoelectric pump 201 is applied across the outer terminals 263 and 272 from the driver circuit 119. Further, with the vibration of the piezoelectric actuator 240, the movable portion 256 of the flexible plate 251 also vibrates. This enables the piezoelectric pump 201 to draw air into the pump chamber 245 via the opening 292 and the suction hole 252. Further, the piezoelectric pump 201 discharges air in the pump chamber 245 through the discharge hole 255.

Here, in the piezoelectric pump 201, a peripheral portion of the piezoelectric actuator 240 is not fixed in a substantial way. Thus, according to the piezoelectric pump 201, a high discharge pressure and a large discharge flow volume are obtained despite of low electric power consumption while reducing loss associating with the vibration of the piezoelectric actuator 240.

Here, the flow volume of gas discharged during one period of pumping at the piezoelectric pump 201 is smaller than the flow volume of gas discharged during one period of pumping at the related art pump that uses a motor, and is 1/200 or less. The flow volume of gas discharged during one period of pumping at the piezoelectric pump 201 is 1 nl or more and 10 μl or less. When the cuff pressure stays within a predetermined range, the flow volume of gas discharged during one period of pumping at the piezoelectric pump 201 is approximately 0.2 μl.

Accordingly, the controller unit 111 can finely regulate the flow volume of gas to be supplied to the cuff 10 with the piezoelectric pump 201 by controlling the driver circuit 119 with the controller unit 111 on the order of milliseconds.

Thus, even in the cuff pressure controller device of the second embodiment, effects similar to the cuff pressure controller device 100 of the first embodiment are achieved.

OTHER EMBODIMENTS

In the foregoing embodiments, air is used as the gas. However, the configuration is not limited thereto. Any gas other than air may also be used as the gas.

Further, in the foregoing embodiments, the piezoelectric element is made of lead zirconate titanate based ceramics, but the configuration is not limited thereto. For example, the piezoelectric element may alternatively be made of a piezoelectric material of non-lead based piezoelectric ceramics such as sodium potassium niobate based ceramics, alkali niobate based ceramics, and the like.

Further, in the foregoing embodiments, a uni-morph type piezoelectric vibrator is used. However, the configuration is not limited thereto. Alternatively, a bimorph type piezoelectric vibrator, in which the piezoelectric elements 40 are provided on both sides of the vibration plate 39, may be used.

Further, in the foregoing embodiments, the disc-shaped piezoelectric element, the disc-shaped vibration plate, and the disc-shaped top plate are used. However, the configuration is not limited thereto. For example, these shapes may alternatively be polygonal plate shapes or elliptical disc shapes.

Further, in the foregoing embodiments, the piezoelectric pump is driven to resonate at the first-order vibration mode frequency (fundamental wave) of the pump main body. However, the configuration is not limited thereto. At time of implementation, the piezoelectric pump may alternatively be driven to resonate at an odd-order vibration mode frequency of the third order vibration mode or higher that has a plurality of anti-nodes.

Further, in the second embodiment, the example is described in which the flexible plate 251 exhibits the bending vibration with the bending vibration of the piezoelectric actuator 240. However, the configuration is not limited thereto. At time of implementation, only the piezoelectric actuator 240 may exhibit the bending vibration, and it may not be always necessary that the flexible plate 251 exhibits the bending vibration in association with the bending vibration of the piezoelectric actuator 240.

In the foregoing embodiments, the check valve 121 is used. However, the configuration is not limited thereto. In a case where the piezoelectric pump has the same non-return capability as the check valve 121, the check valve 121 may be omitted.

Lastly, it is to be understood that the foregoing descriptions of the embodiments are exemplary in all aspects and are not restrictive. The scope of the present disclosure is defined by the scope of claims and not by the foregoing embodiments. Furthermore, in the scope of the present disclosure, all variations which come within the meaning and range of equivalency of the claims are therefore intended to be embraced therein.

1 Intubation tube
2 Trachea
3 Esophagus
4 Epiglottis
5 Cavity of mouth
8 Inner wall
10 Cuff
17 Outer casing
18 Nozzle
24 Discharge hole
31 Ventilation path
36 Pump chamber
37 Top plate
38 Side plate
39 Vibration plate 40 Piezoelectric element
42 Cap
45 Ventilation hole
52 Projection portion
53 Suction opening
55A Cutout
56A Screw hole
61 Center portion
62 Projection portion
63 Outer terminal
63, 72 Outer terminal
70 Electrode conduction plate
72 Outer terminal
73 Inner terminal
90 Cuff
100 Cuff pressure controller device
101 Piezoelectric pump
111 Controller unit
112 Memory unit
113 Cuff pressure detector unit
114 Input unit
115 Display unit
116 Speaker unit
118 Cuff pressure detection tube
119 Driver circuit
121 Check valve
122 Release valve
125 Air supply tube
201 Piezoelectric pump
240 Piezoelectric actuator
241 Vibration plate
242 Piezoelectric element
243 Reinforcing plate
245 Pump chamber
251 Flexible plate
252 Suction hole
253A, 253B, 253C Spacer
254 Cover plate
255 Discharge hole
256 Movable portion
257 Fixed portion
260 Vibration plate unit
261 Frame plate
262 Joint portion
263 Outer terminal
270 Electrode conduction plate
271 Frame portion
272 Outer terminal
273 Inner terminal
280 Pump casing
291 Substrate
292 Opening
900 Cuff pressure controller device
910 Control system
911 Controller unit
913 Cuff pressure detector unit
916 Alarm unit
918 Cuff pressure detection tube
920 Cuff pressure regulator unit
921 Unidirectional valve
922 Release valve
923 Flow volume regulator valve
924 Reservoir tank
925 Gas supply tube
926 Pressure pump
927 Safety valve

The invention claimed is:

1. A cuff pressure controller device comprising:
a pump that includes a discharge hole connected to a cuff and discharges gas from the discharge hole to the cuff wherein an air supply tube connecting the pump to the cuff is free of a flow volume regulator valve;
a cuff pressure detector unit that detects pressure inside the cuff;
a driver circuit that drives the pump at a drive frequency of 15 kHz or higher; and
a controller unit that controls the driver circuit in such a way that the pressure inside the cuff stays within a predetermined range based on a detection result from the cuff pressure detector unit.

2. The cuff pressure controller device according to claim 1, wherein
a flow volume of the gas discharged during one period of pumping by the pump is 1 nl or more and 10 µl or less.

3. The cuff pressure controller device according to claim 2, wherein
the drive frequency is a resonant frequency of the pump.

4. The cuff pressure controller device according to claim 2, wherein
the pump includes a piezoelectric element as an actuator and a vibration plate that has a first principal surface to which the piezoelectric element is joined, and the vibration plate exhibits a bending vibration due to expansion and contraction of the piezoelectric element.

5. The cuff pressure controller device according to claim 2, wherein
the controller unit controls the driver circuit at a control frequency that is equal to or less than one-tenth of the drive frequency.

6. The cuff pressure controller device according to claim 2, further comprising:
a check valve provided between the discharge hole of the pump and the cuff for preventing an outflow of the gas from the cuff to the discharge hole; and
a release valve connected to the cuff for releasing the gas filled in the cuff.

7. The cuff pressure controller device according to claim 1, wherein
the drive frequency is a resonant frequency of the pump.

8. The cuff pressure controller device according to claim 7, wherein
the pump includes a piezoelectric element as an actuator and a vibration plate that has a first principal surface to which the piezoelectric element is joined, and the vibration plate exhibits a bending vibration due to expansion and contraction of the piezoelectric element.

9. The cuff pressure controller device according to claim 7, wherein
the controller unit controls the driver circuit at a control frequency that is equal to or less than one-tenth of the drive frequency.

10. The cuff pressure controller device according to claim 7, further comprising:
a check valve provided between the discharge hole of the pump and the cuff for preventing an outflow of the gas from the cuff to the discharge hole; and
a release valve connected to the cuff for releasing the gas filled in the cuff.

11. The cuff pressure controller device according to claim 1, wherein
the pump further includes a piezoelectric element as an actuator and a vibration plate that has a first principal surface to which the piezoelectric element is joined, and the vibration plate exhibits a bending vibration due to expansion and contraction of the piezoelectric element.

12. The cuff pressure controller device according to claim 11, wherein
the pump includes
a first casing that is joined to the vibration plate and constitutes a pump chamber together with the vibration plate, and
a second casing that covers the first casing with a gap therebetween and forms a ventilation path between the first casing and the second casing, wherein
the first casing is provided with a ventilation hole that allows inside of the pump chamber to communicate with outside of the pump chamber, and the discharge hole is formed in the second casing at an area opposite to the ventilation hole.

13. The cuff pressure controller device according to claim 11, wherein
the pump includes
a frame plate that surrounds the vibration plate;
a joint portion that joins the vibration plate and the frame plate and elastically supports the vibration plate relative to the frame plate, and
a flexible plate joined to the frame plate so as to oppose a second principal surface of the vibration plate located at an opposite side of the first principal surface, the flexible plate being provided with a ventilation hole.

14. The cuff pressure controller device according to claim 11, wherein
the controller unit controls the driver circuit at a control frequency that is equal to or less than one-tenth of the drive frequency.

15. The cuff pressure controller device according to claim 11, further comprising:
a check valve provided between the discharge hole of the pump and the cuff for preventing an outflow of the gas from the cuff to the discharge hole; and
a release valve connected to the cuff for releasing the gas filled in the cuff.

16. The cuff pressure controller device according to claim 1, wherein
the controller unit controls the driver circuit at a control frequency that is equal to or less than one-tenth of the drive frequency.

17. The cuff pressure controller device according to claim 16, further comprising:
a check valve provided between the discharge hole of the pump and the cuff for preventing an outflow of the gas from the cuff to the discharge hole; and
a release valve connected to the cuff for releasing the gas filled in the cuff.

18. The cuff pressure controller device according to claim 16, wherein
the pump includes
a first casing that is joined to a vibration plate and constitutes a pump chamber together with the vibration plate, and
a second casing that covers the first casing with a gap therebetween and forms a ventilation path between the first casing and the second casing, wherein
the first casing is provided with a ventilation hole that allows inside of the pump chamber to communicate with outside of the pump chamber, and the discharge hole is formed in the second casing at an area opposite to the ventilation hole.

19. The cuff pressure controller device according to claim 1, further comprising:
a check valve provided between the discharge hole of the pump and the cuff for preventing an outflow of the gas from the cuff to the discharge hole; and
a release valve connected to the cuff for releasing the gas filled in the cuff.

20. The cuff pressure controller device according to claim 19, wherein
the pump includes
a first casing that is joined to a vibration plate and constitutes a pump chamber together with the vibration plate, and
a second casing that covers the first casing with a gap therebetween and forms a ventilation path between the first casing and the second casing, wherein
the first casing is provided with a ventilation hole that allows inside of the pump chamber to communicate with outside of the pump chamber, and the discharge hole is formed in the second casing at an area opposite to the ventilation hole.

* * * * *